(12) United States Patent
Felemban et al.

(10) Patent No.: US 12,718,933 B2
(45) Date of Patent: Aug. 25, 2026

(54) SYSTEMS AND METHODS FOR BUILDING HEALTHCARE NETWORKS

(71) Applicant: MCKINSEY & COMPANY, INC., New York, NY (US)

(72) Inventors: Nawaf Felemban, Washington, DC (US); Christopher E. Haddad, Denver, CO (US)

(73) Assignee: MCKINSEY & COMPANY, INC., New York, NY (US)

( * ) Notice: Subject to any disclaimer, the term of this patent is extended or adjusted under 35 U.S.C. 154(b) by 0 days.

(21) Appl. No.: 17/974,493

(22) Filed: Oct. 26, 2022

(65) Prior Publication Data

US 2024/0145069 A1 May 2, 2024

(51) Int. Cl.
*G16H 40/20* (2018.01)
*G06N 20/00* (2019.01)
*G16H 50/20* (2018.01)

(52) U.S. Cl.
CPC ............ *G16H 40/20* (2018.01); *G06N 20/00* (2019.01)

(58) Field of Classification Search
CPC .............................. G16H 40/20; G06N 20/00
See application file for complete search history.

(56) References Cited

U.S. PATENT DOCUMENTS

| | | | | |
|---|---|---|---|---|
| 10,997,244 | B2 * | 5/2021 | Russell | G06F 21/56 |
| 11,328,825 | B1 * | 5/2022 | Yu | G16H 50/20 |
| 2021/0174968 | A1 * | 6/2021 | Butterfield | G06F 18/2135 |
| 2022/0067841 | A1 * | 3/2022 | Hanson | G16H 40/20 |
| 2022/0188693 | A1 * | 6/2022 | Tommasi | G06N 5/022 |
| 2022/0359067 | A1 * | 11/2022 | McCallum | G06Q 30/0206 |
| 2024/0006058 | A1 * | 1/2024 | Dare | G16H 50/20 |

* cited by examiner

*Primary Examiner* — Maroun P Kanaan
(74) *Attorney, Agent, or Firm* — MARSHALL, GERSTEIN & BORUN LLP; William J. Samore

(57) ABSTRACT

The present disclosure generally relates to building healthcare provider networks. In some embodiments, mini healthcare provider networks may be built using historical healthcare provider data. The mini healthcare provider networks may then be used to train a machine learning algorithm. Potential healthcare provider data may then be received, and input into the trained machine learning algorithm to determine a healthcare provider network.

20 Claims, 4 Drawing Sheets

| 310 Category | 320 Datasets | 330 Use in Optimization |
|---|---|---|
| Cost | - claims from procedures<br>- price transparency | Calculate INN/OON utilization and risk-adjusted cost efficiency |
| Quality of care | - HCAHPS; STARS; HEDIS<br>- custom metrics<br>- scraped reviews/ratings | Assess care quality and member satisfaction to prioritize between providers |
| Competitor network affiliation | - public use files (PUF)<br>- scraped directory<br>- PPES NPI registry | Maximize competitor network disruption (i.e. loss of in-network providers upon switching to competitor) |
| Population data | - detailed demographic data (e.g. age, income, employment)<br>- chronic disease prevalence | Meet specific population needs (Medicare, Medicaid, specialty by disease prevalence) and ensure equitable access to care |
| Geographic | - processed Census shape files (boundaries, adjacency, distances)<br>- Census area to zip cross walks | Perform geospatial analytics |
| Access standards | - Line of business access standards (e.g. Medicare) specifying maximum distance/drive time to providers | Ensure line-of-business specific adequacy standards are met |

SYSTEMS AND METHODS FOR BUILDING HEALTHCARE NETWORKS

FIELD

The present disclosure generally relates to building healthcare provider networks, and more particularly relates to using artificial intelligence (AI) to build healthcare provider networks.

BACKGROUND

Health insurance companies face the challenging task of developing networks of healthcare providers to offer to their customers. In the past, such networks of healthcare providers were developed simply by including every possible healthcare provider in the network although not all approaches were successful at (a) identifying every provider, or (b) reaching a contractual agreement with each party in the proposed healthcare network. Indeed, some healthcare provider networks were developed with a philosophy of "broader is better." However, over time it was learned that there were drawbacks to building healthcare provider networks this way. For example, this approach did not yield affordable, equitable and high quality networks.

The systems and methods disclosed herein provide solutions to this problem and others, and may provide solutions to other drawbacks of conventional techniques.

SUMMARY

In one aspect, a computer-implemented method for building a healthcare provider network may be provided. The method may include: (1) receiving, via one or more processors, historical healthcare provider data; (2) training, via the one or more processors, a machine learning algorithm based on the historical healthcare provider data; (3) receiving, via the one or more processors, potential healthcare provider data, the potential healthcare provider data including data of individual healthcare providers, and healthcare provider facilities; and (4) building, via the one or more processors, a healthcare provider network by inputting the potential healthcare provider data into the trained machine learning algorithm.

In another aspect, a computer-implemented method for building a healthcare provider network may be provided. The method may include: (1) receiving, via the one or more processors, potential healthcare provider data, the potential healthcare provider data including data of individual healthcare providers, and healthcare provider facilities; and (2) building, via the one or more processors, a healthcare provider network by inputting the potential healthcare provider data into the trained machine learning algorithm, wherein the built healthcare provider network includes individual healthcare providers and healthcare provider facilities.

In yet another aspect, a computer system configured to build a healthcare provider network may be provided. The computer system may include one or more processors configured to: (1) receive historical healthcare provider data; (2) train a machine learning algorithm based on the historical healthcare provider data; (3) receive potential healthcare provider data, the potential healthcare provider data including data of individual healthcare providers, and healthcare provider facilities; and (4) build a healthcare provider network by inputting the potential healthcare provider data into the trained machine learning algorithm.

BRIEF DESCRIPTION OF THE DRAWINGS

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

The figures described below depict various aspects of the applications, methods, and systems disclosed herein. It should be understood that each figure depicts an embodiment of a particular aspect of the disclosed applications, systems and methods, and that each of the figures is intended to accord with a possible embodiment thereof. Furthermore, wherever possible, the following description refers to the reference numerals included in the following figures, in which features depicted in multiple figures are designated with consistent reference numerals.

FIG. 3 shows an example illustration of healthcare provider data.

DETAILED DESCRIPTION

To provide high quality healthcare insurance to patients, healthcare insurance companies must develop networks of healthcare providers. This is a difficult task, as including too few healthcare providers may leave customers out of a network of their preferred healthcare provider; but including too many healthcare providers may produce a higher cost network, resulting in increased healthcare insurance premiums. Another danger is that including too many healthcare providers may result in a lower quality network, as some of the providers included might be of low quality resulting in worse outcomes for patients. Furthermore, some healthcare providers may bring both benefits and drawbacks to a healthcare provider network (e.g., a physician provides a high quality of care, but also charges a large fee per visit), making it difficult to tell if the particular healthcare provider should be added to a particular network. Still further, governmental regulations of healthcare provider networks vary greatly by region of the country (e.g., although Medicare is federally mandated so the regulations are nationally uniform, commercial, Medicaid and affordable care act (ACA) exchange are state-regulated so there are regulations for each state, etc.), thus making it even more complicated for insurance companies to build networks of healthcare providers.

The systems and methods disclosed herein solve these challenges and others by training a machine learning algorithm to build healthcare provider networks.

Example System for Building Healthcare Provider Networks

Figure 1:
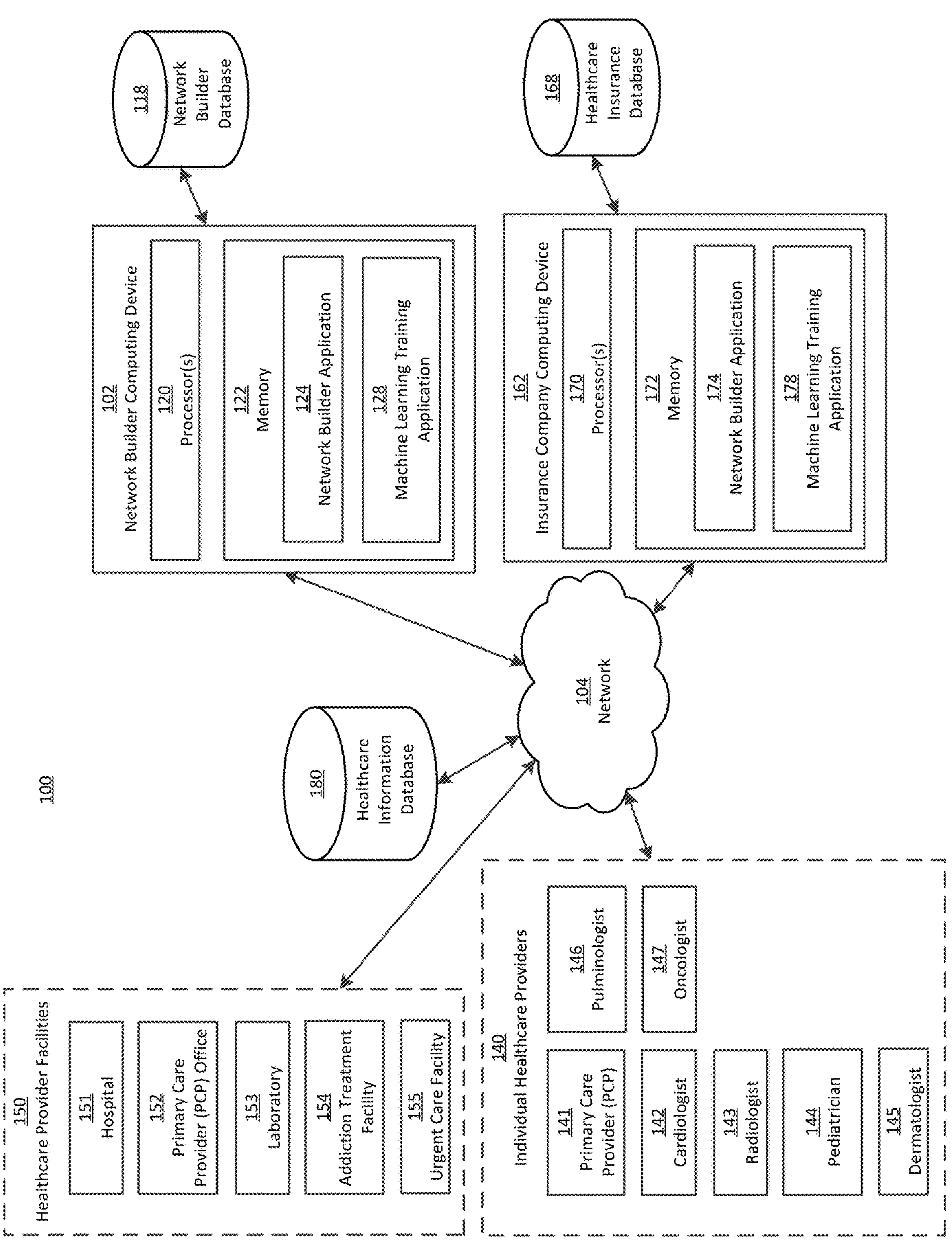
FIG. 1 illustrates an example system for building healthcare provider networks.

FIG. 1 illustrates an example computer system 100 for building healthcare provider networks. The high-level architecture illustrated in FIG. 1 may include both hardware and software applications, as well as various data communications channels for communicating data between the various hardware and software components, as is described below.

The system 100 may include a network builder computing device 102 to build the healthcare provider networks. In some embodiments, the network builder computing device 102 is not owned by a healthcare insurance company, and rather is owned by a third party that has been contracted by a healthcare insurance company to build an optimal healthcare provider network.

The network builder computing device 102 may include one or more processors 120, such as one or more microprocessors, controllers, and/or any other suitable type of processor. For example, the one or more processors 120 may be any combination of central processing units (CPUs) and/or graphics processing units (GPUs). The network builder computing device 102 may further include a memory 122 (e.g., volatile memory, non-volatile memory) accessible by the one or more processors 120, (e.g., via a memory controller).

The one or more processors 120 may interact with the memory 122 to obtain, for example, computer-readable instructions stored in the memory 122. Additionally or alternatively, computer-readable instructions may be stored on one or more removable media (e.g., a compact disc, a digital versatile disc, removable flash memory, etc.) that may be coupled to the network builder computing device 102 to provide access to the computer-readable instructions stored thereon. Additionally or alternatively, the computer-readable instructions may be stored in cloud storage. In particular, the computer-readable instructions stored on the memory 122 may include instructions for executing various applications, such as a network builder application 124, and/or a machine learning training application 128.

In general, the machine learning training application 128 may train a machine learning algorithm to build healthcare provider networks; and the network builder application 124 may use the trained machine learning algorithm to build healthcare provider networks. Either or both of the trained machine learning algorithm, and/or any built healthcare provider networks may be stored in the memory 122 and/or the network builder database 118.

The healthcare provider networks, such as those built by the network builder application 124, may include healthcare provider facilities 150. Examples of the healthcare provider facilities 150 include hospital 151, primary care provider (PCP) office 152, laboratory 153, addiction treatment facility 154, and urgent care facility 155. It should be understood that although the example system 100 illustrates one of each of the hospital 151, primary care provider (PCP) office 152, laboratory 153, addiction treatment facility 154, and urgent care facility 155, any number of any of these healthcare provider facilities may be included in any system, and/or in any healthcare provider network.

Additionally or alternatively, the healthcare provider networks may include individual healthcare providers 140. Examples of the individual healthcare providers include a PCP 141, a cardiologist 142, a radiologist 143, a pediatrician 144, a dermatologist 145, a pulmonologist 146, and an oncologist 147. It should be understood that although the example system 100 illustrates one of each of the PCP 141, cardiologist 142, radiologist 143, pediatrician 144, dermatologist 145, pulmonologist 146, and oncologist 147, any number of any of these individual healthcare providers may be included in any system, and/or in any healthcare provider network.

To train the machine learning algorithm, and/or to build the healthcare provider networks, the network builder computing device 102 may receive data from healthcare information database 180. The healthcare information database 180 may store any suitable data. Examples of the data stored by the healthcare information database include patient data (e.g., patient name, gender, age, income, address, phone number, email, etc.), healthcare history data of patients, insurance records, healthcare provider facility information (e.g., cost information of the healthcare provider facility, efficiency of the healthcare provider facility (e.g., information of if patients have to repeat visits), reviews of the healthcare provider facilities, quality of care ratings of the healthcare provider facilities, affiliation data (e.g., what individual healthcare providers the healthcare provider facilities are associated with), classification of the healthcare provider facility (e.g., classified based on average income of a population where the healthcare facility is located, classified based on an urban to rural scale, etc.), etc.), and individual healthcare provider data (e.g., age of the individual healthcare provider, gender of the individual healthcare provider, race of the individual healthcare provider, languages spoken by the individual healthcare provider, specialties of the individual healthcare provider, certifications of the individual healthcare provider, educational background of the individual healthcare provider, years of experience of the individual healthcare provider, member satisfaction ratings of the individual healthcare provider, cost information of the individual healthcare provider, efficiency of the individual healthcare provider (e.g., information of if patients have to repeat visits), reviews of the individual healthcare provider, quality of care ratings of the individual healthcare providers, affiliation data (e.g., what healthcare provider facilities are associated with the individual healthcare providers, etc.), population data (e.g., average income, poverty levels, housing information, etc. of a population of a geographic area), etc.).

In some examples, the healthcare information database 180 is a governmental database (e.g., a census database, a city database, a Centers for Medicare & Medicaid Services (CMS) database, a state's Department of Health database, etc.). In other examples, the healthcare information database 180 is a database of a third-party aggregator that aggregates information, such as medical records, healthcare records, insurance claims data, payer provider directories, etc. Furthermore, although the example system 100 illustrates only one healthcare information database 180, any number of healthcare information databases 180 may be included.

The example system 100 also includes insurance company computing device 162, which may provide any kind of insurance (e.g., healthcare insurance, dental insurance, vision insurance, life insurance, etc.). In some examples the insurance company owning the insurance company computing device 162 contracts a company owning the network builder computing device 102 to build healthcare provider networks (e.g., by training and/or applying a machine learning algorithm). Additionally or alternatively, the insurance company computing device 162 itself may build the healthcare provider networks (e.g., by training and/or applying a machine learning algorithm). The insurance company computing device 162 may also anonymize any of the data that it holds (e.g., insurance claims data).

The insurance company computing device 162 may include one or more processors 170 such as one or more microprocessors, controllers, and/or any other suitable type of processor. For example, the one or more processors 170 may be any combination of central processing units (CPUs) and/or graphics processing units (GPUs). The insurance company computing device 162 may further include a memory 172 (e.g., volatile memory, non-volatile memory) accessible by the one or more processors 170, (e.g., via a memory controller).

The one or more processors 170 may interact with the memory 172 to obtain, for example, computer-readable instructions stored in the memory 172. Additionally or alternatively, computer-readable instructions may be stored on one or more removable media (e.g., a compact disc, a digital versatile disc, removable flash memory, etc.) that may be coupled to the insurance company computing device 162 to provide access to the computer-readable instructions stored thereon. In particular, the computer-readable instructions stored on the memory 172 may include instructions for executing various applications, such as a network builder application 174, and/or a machine learning training application 178.

In general, the machine learning training application 178 may train a machine learning algorithm to build healthcare provider networks; and the network builder application 174 may use the trained machine learning algorithm to build healthcare provider networks. Either or both of the trained machine learning algorithm, and/or any built healthcare provider networks may be stored in the memory 172 and/or the healthcare insurance database 168.

Furthermore, the example system 100 includes network 104 (which may be a wired or wireless network, such as the Internet), which allows the components of the example system 100 to communicate with each other.

Moreover, although the example of FIG. 1 illustrates only one of each of many of the components, such as the network builder computing device 102, the healthcare information database 180, the healthcare provider facilities 150 (e.g., hospital 151, PCP office 152, laboratory 153, addiction treatment facility 154, urgent care facility 155 etc.), the individual healthcare providers 140 (e.g., PCP 141, cardiologist 142, radiologist 143, pediatrician 144, dermatologist 145, pulmonologist 146, oncologist 147, etc.), etc., any number of each of the components illustrated in FIG. 1 may be included in a system (e.g., multiple healthcare information databases 180, multiple PCPs 141, etc.).

Construction of Example Healthcare Provider Networks

The healthcare provider networks may be built by machine learning algorithm(s) trained by one or both of the machine learning training applications 128, 178, and/or applied by one or both of the network builder applications 124, 174. In this regard, although the following discussion refers to the network builder computing device 102 as performing the example steps, it should be understood that any of the steps may be performed by the insurance company computing device 162 as well. Furthermore, it should be understood that although the following discussion refers to a single machine learning algorithm, the techniques may also be applied to training multiple machine learning algorithms to build healthcare provider networks.

Figure 2:
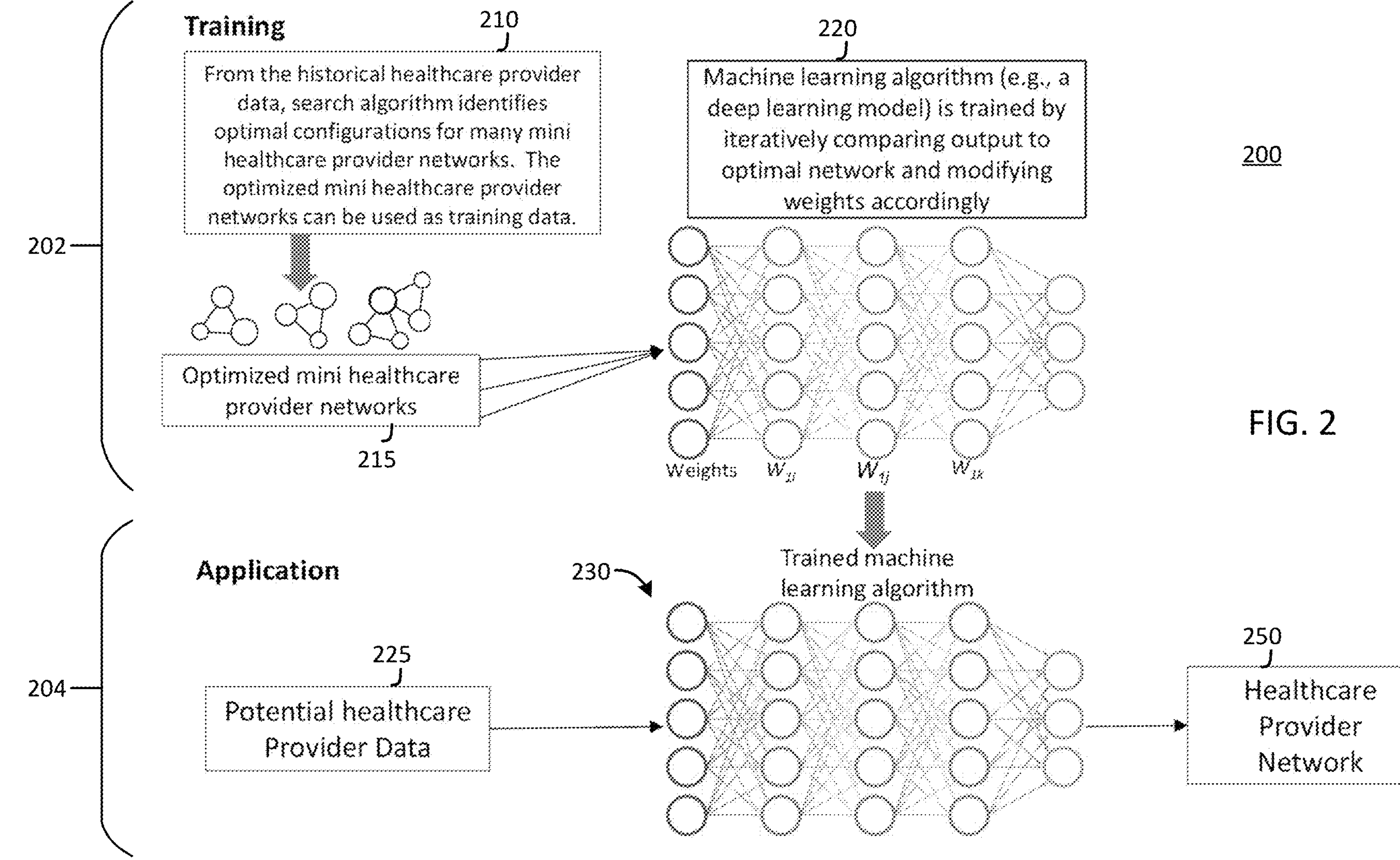
FIG. 2 shows an example overview flowchart for building a healthcare provider network.

Broadly speaking, FIG. 2 shows an example overview flowchart 200 for building a healthcare provider network, wherein the example flowchart 200 includes a training phase 202 and an application phase 204.

Beginning with the training phase 202, in some embodiments, the machine learning algorithm may be trained based on historical healthcare provider data (e.g., received by the network builder computing device 102). More specifically, in the example of FIG. 2, at 210, the network builder computing device 102 may identify, from the historical healthcare provider data and/or forecasted healthcare provider data, "optimal" healthcare provider networks. In some implementations, the optimal healthcare provider networks are mini healthcare provider networks identified by a search algorithm (e.g., depth first search) on a small subset of markets. As used herein, "mini" healthcare provider network means a healthcare provider network that is smaller than the healthcare provider network that the machine learning algorithm will build (e.g., the full healthcare provider network). In one example, if the goal is to build a large (e.g., full) healthcare provider network (e.g., for Los Angeles), the optimal healthcare provider networks (e.g., the mini healthcare provider networks) identified in the historical data may be smaller healthcare provider networks (e.g., from sections of Los Angeles or from sections of any other city).

The mini healthcare provider networks may be optimized based on any suitable criteria. FIG. 3 shows an example illustration 300 of healthcare provider data. Any of the data illustrated in the example of FIG. 3 may be included in the historical healthcare provider data, and used to build the mini healthcare provider networks. In addition, as discussed elsewhere herein, any of the data illustrated in the example of FIG. 3 may be included in the potential healthcare provider data that is used to build the healthcare provider network (e.g., the full healthcare provider network).

The example illustration 300 shows that the healthcare provider data may be divided into categories 310. Thus, as this shows, examples of data that the mini healthcare provider networks may be optimized based on include: cost, quality of care, member experience, competitor network affiliation, population data, geographic data, social determinants of health data, and access standards data. Datasets 320 illustrates further detail of each of the categories 310. And, use in optimization 330 illustrates examples of uses for optimization (e.g., of the mini healthcare provider network or healthcare provider network).

To optimize the mini healthcare provider networks, the search algorithm may maximize an objective cost function that maximizes along a number of dimensions from the historical healthcare provider data (e.g., cost, quality of care, member experience, competitor network affiliation, population data, geographic data, social determinants of health data, access standards data, etc., as illustrated in the example of FIG. 3).

In some example implementations, the search algorithm used to identify the mini healthcare provider networks is depth-first search (e.g., an algorithm for searching tree or graph data structures, which starts at a root node, and searches as far as possible along each branch before backtracking). In other example implementations, the search algorithm used to identify the mini healthcare provider networks is breadth-first search (e.g., an algorithm for searching graph or tree data structures, which starts at a root node, and searches all nodes at a present depth before moving on to nodes at a next depth level). However, these are only examples, and any search algorithm(s) may be used. Furthermore, any of the search algorithms (including depth-first search and breadth-first search) may use the optimization function described above.

In some aspects, using a search algorithm, such as depth-first search, breadth-first, or any exhaustive search algorithm, would take, as a practical matter, too long to identify a full healthcare provider network (since complexity increases nonlinearly). However, as described herein, using the search algorithm to build mini healthcare provider networks allows for a scalable machine learning algorithm to be trained. In this regard, advantageously, training the machine learning algorithm using such mini medical provider networks allows the trained machine learning algorithm to quickly identify the optimal healthcare provider network configuration (e.g., build the healthcare provider network) while taking into account wide range of constraints.

Furthermore, in some implementations, the mini healthcare provider networks are created from existing markets. Specifically, some embodiments use some proportion of zip code aggregations (e.g., ZIP-3s), using techniques during sampling and training to ensure a representative sample of various characteristics (urban vs rural, states, etc.). In some embodiments, the mini healthcare provider networks may be geographically overlapping with each other.

Once the mini healthcare provider networks are constructed/optimized, at 215, the network builder computing device 102 uses the optimized mini healthcare provider networks to begin to train the machine learning algorithm. In some examples, the machine learning algorithm is a deep learning algorithm; which, in some implementations, uses heuristics—such as tabu search, guided local search, ant colony, and Lin-Kernighan—to calculate optimal healthcare provider networks for select geographies using a wide range of constraints. However, these are only examples, and any kind of machine learning algorithm with any kind of heuristics may be used.

At 220, the network builder computing device 102 continues to train the machine learning algorithm by iteratively comparing output to optimal network(s) (e.g., the optimal mini healthcare provider networks), and optimizing the weights (e.g., $W_{1i}$, $W_{1j}$, $W_{1k}$, etc., in the example of FIG. 2).

Once the training is complete, the final machine learning algorithm may be output. Any suitable set of criteria may be used to determine that the training is complete. For example, accuracy metrics generated during event 220 may be used to determine if the training is complete.

During the application phase 204, the network builder computing device 102 may receive potential healthcare provider data at 225. The potential healthcare provider data may be data of healthcare providers (e.g., individual healthcare providers 140, healthcare provider facilities 150, etc.) corresponding to a specified geographic area (e.g., Los Angeles). In this regard, the potential healthcare provider data may be data of all healthcare providers that could potentially be added to the healthcare provider network.

The potential healthcare provider data may include any of the kinds of data discussed above with respect to the historical healthcare provider data (e.g., cost, quality of care, competitor network affiliation, population data, geographic data, access standards data, etc., as illustrated in the example of FIG. 3).

The potential healthcare provider data may then, at 230, be input into the trained machine learning algorithm, which may output the healthcare provider network at 250.

Furthermore, it has been found that training and applying the machine learning algorithm on a GPU advantageously decreases the amount of time that it takes to train and apply the machine learning algorithm as compared to training and applying the machine learning algorithm on a CPU.

Examples of Healthcare Provider Networks

As described herein, the healthcare provider networks may be built by one or both of the network builder computing device 102, and/or the insurance company computing device 162). Examples of healthcare provider networks include health insurance networks, medical insurance networks, dental insurance networks, and vision insurance networks. In some embodiments, the healthcare provider networks may be built for a specific geographic area (e.g., a city, a state, other jurisdiction, etc.).

In some embodiments, the healthcare provider networks include individual healthcare providers 140. The individual healthcare providers 140 may have types, such as PCPs 141, cardiologists 142, radiologists 143, pediatricians 144, dermatologists 145, pulmonologists 146, oncologists 147, etc. Advantageously, the machine learning algorithm may build (or be trained to build) healthcare provider networks emphasizing any of these types of individual healthcare providers. For example, the machine learning algorithm may build a healthcare provider network with a disproportionately large number of PCP providers compared to other types of individual healthcare providers (e.g., a "PCP heavy network"). In one example of this, if the ratio of PCPs to other types of providers is X:Y in other healthcare provider networks, then a healthcare provider network with a disproportionately large number of PCP providers may have a ratio of X*Z:Y, where Z>1.

In another example, advantageously, the machine learning algorithm may build (or be trained to build) healthcare provider networks with requirements for provider-to-population ratios, such as a requirement of a provider-to-population ratio of greater than a predefined number. For example, a network may be built with a requirement to include a ratio of PCP:1000 people of at least 12. In another example, a network may be built with a requirement to include a ratio of orthopedists:1000 people of at least 5.

In some embodiments, the healthcare provider networks include healthcare provider facilities 150. The healthcare provider facilities may have types, such as hospital 151, PCP office 152, laboratory 153, addiction treatment facility 154, urgent care facility 155, etc. Advantageously, the machine learning algorithm may build (or be trained to build) healthcare provider networks emphasizing any of these types of healthcare provider facilities. For example, the machine learning algorithm may build a healthcare provider network with a disproportionately large number of urgent care facilities compared to other types of healthcare provider facilities. In one example of this, if the ratio of urgent care facilities to other types healthcare provider facilities is X:Y in other healthcare provider networks, then a healthcare provider network with a disproportionately large number of urgent care facilities may have a ratio of X*Z:Y, where Z>1.

In some embodiments, the healthcare provider networks also may include healthcare organizations (e.g., Cleveland Clinic, etc.). Examples of healthcare organizations include hospital systems, laboratory systems, etc.

The healthcare provider networks themselves may also have types. For example, a healthcare provider network may be a Medicare network, a Medicaid network, an exchange network, etc. As such, the machine learning algorithm may be trained to build each type of healthcare provider network.

The healthcare provider networks may also have an organization type. Examples of the organization type include health maintenance organization (HMO), and preferred provider organization (PPO). As such, the machine learning algorithm may be trained to build healthcare provider networks of each organization type.

The healthcare provider networks may also be single tier networks or tiered networks. In this regard, the machine learning algorithm may be trained to build one or both of single tier networks or tiered networks.

Example Methods

Figure 4:
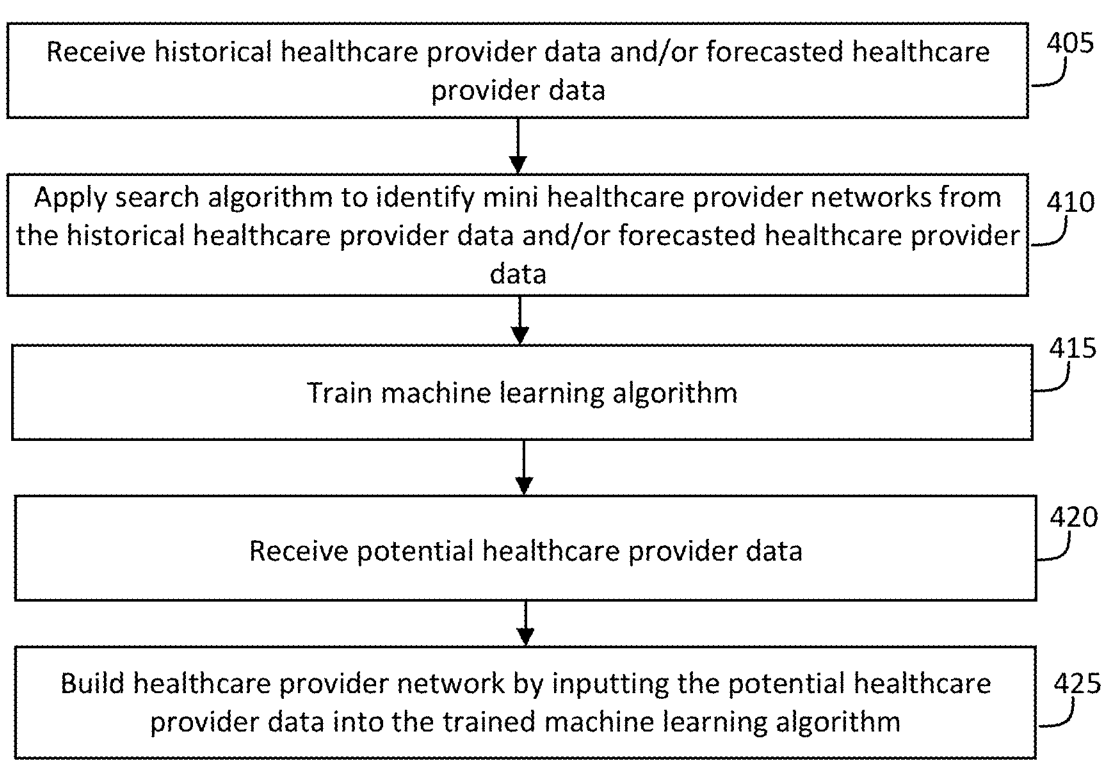
FIG. 4 shows an example method of building a healthcare provider network.

FIG. 4 shows an example method 400 of building a healthcare provider network. Although, for illustrative purposes, the following discussion will refer to the one or more processors 120 of the network builder computing device 102 as performing the blocks of the method 400, it should be understood that any other component (e.g., the one or more processors 170 of the insurance company computing device 162, etc.) may perform any of the blocks instead of or in conjunction with the one or more processors 120.

The example method 400 begins at block 405 when the one or more processors 120 receive historical healthcare provider data. The historical healthcare provider data may be received from any source, or combination of sources. For example, the historical healthcare provider data may be received from the insurance company computing device 162, the healthcare information database 180, the network builder database 118, any of the healthcare provider facilities 150 (e.g., hospital 151, PCP office 152, laboratory 153, addiction treatment facility 154, urgent care facility 155 etc.), any of the individual healthcare providers 140 (e.g., PCP 141, cardiologist 142, radiologist 143, pediatrician 144, dermatologist 145, pulmonologist 146, oncologist 147, etc.), etc. Furthermore, the historical healthcare provider data may be received from any combination of these example sources.

In some examples, the historical healthcare provider data may include any of the data discussed above with respect to FIG. 3 (e.g., cost, quality of care, member experience, competitor network affiliation, population data, geographic data, social determinants of health data, access standards data, etc.). Additionally or alternatively, the historical healthcare provider data may include patient data (e.g., patient name, gender, age, income, address, phone number, email, etc.), healthcare history data of patients, insurance records, healthcare provider facility information (e.g., cost information of the healthcare provider facility, efficiency of the healthcare provider facility (e.g., information of if patients have to repeat visits), reviews of the healthcare provider facilities, quality of care ratings of the healthcare provider facilities, affiliation data (e.g., what individual healthcare providers the healthcare provider facilities are associated with), classification of the healthcare provider facility (e.g., classified based on average income of a population where the healthcare facility is located, classified based on an urban to rural scale, etc.), etc.), individual healthcare provider data (e.g., age of the individual healthcare provider, gender of the individual healthcare provider, race of the individual healthcare provider, languages spoken by the individual healthcare provider, specialties of the individual healthcare provider, certifications of the individual healthcare provider, educational background of the individual healthcare provider, years of experience of the individual healthcare provider, member satisfaction ratings of the individual healthcare provider, cost information of the individual healthcare provider, efficiency of the individual healthcare provider (e.g., information of if patients have to repeat visits), reviews of the individual healthcare provider, quality of care ratings of the individual healthcare providers, affiliation data (e.g., what healthcare provider facilities are associated with the individual healthcare providers, etc.), population data (e.g., average income, poverty levels, housing information, etc. of a population of a geographic area), etc.), and census data.

In some embodiments, the one or more processors edits or refines the historical healthcare provider data. For example, in some embodiments, the one or more processors may assign cost efficiency metrics to individual healthcare providers based on readmission rates, negotiated rates, utilization, measures of preventable adverse events, and/or number of recommended tests. For example, if an individual healthcare provider recommends excessively many (and possibly unnecessary) tests, the individual healthcare provider may have a lower cost efficiency metric.

Additionally or alternatively to receiving the historical healthcare provider data, the one or more processors 120 may receive forecasted healthcare provider data (e.g., from any of the sources that may send the healthcare provider data. The forecasted data may include, for example, expected increases or decreases (or expected rate of increases or decreases) in pricing for certain healthcare services. In one example, the forecasted data includes an expected price increase in pulmonology services.

At block 410, the one or more processors 120 apply a search algorithm to the received historical healthcare provider data and/or forecasted healthcare provider data to identify optimized mini healthcare provider networks. However, in some embodiments, the mini healthcare provider networks have already been identified in the received historical healthcare provider data; and thus, in some embodiments, block 410 is not performed.

At block 415, the one or more processors 120 train a machine learning algorithm. The machine learning algorithm may be trained by any suitable technique, and based on any suitable data. For example, the machine learning algorithm may be trained using the mini healthcare provider networks as input data. Additionally or alternatively, the machine learning algorithm may be trained based on the historical healthcare provider data and/or forecasted healthcare provider data.

Some embodiments include, during training at block 415, applying one or more requirements such that the trained machine learning algorithm will build a healthcare provider network with the requirement. For example, some requirements may be applied to increase accessibility. For instance, an applied requirement may be that a healthcare provider network built by the machine learning algorithm include a larger healthcare facility density for a geographic area with higher population density than for a geographic area with a lower population density.

Other examples of requirements may be requirements to increase equity. For instance, an applied requirement may be that a healthcare provider network built by the machine learning algorithm include a higher density of healthcare facilities for a geographic area with a lower income population than a density of healthcare facilities for a geographic area with a higher income population.

Still other examples of requirements may be requirements to meet governmental regulations. For example, there may be a governmental requirement to include a particular number of PCPs in a healthcare provider network based on a population density.

At block 420, the one or more processors 120 may receive potential healthcare provider data. In one example, the potential healthcare provider data may be data of all healthcare providers that could potentially be added to the healthcare provider network.

In some examples, the potential healthcare provider data may include any of the data discussed above with respect to FIG. 3 (e.g., cost, quality of care, competitor network affiliation, population data, geographic data, access standards data, etc.). Additionally or alternatively, the potential healthcare provider data may include patient data (e.g., patient name, gender, age, income, address, phone number, email, etc.), healthcare history data of patients, insurance records, healthcare provider facility information (e.g., cost information of the healthcare provider facility, efficiency of the healthcare provider facility (e.g., information of if patients have to repeat visits), reviews of the healthcare provider facilities, quality of care ratings of the healthcare provider facilities, affiliation data (e.g., what individual healthcare providers the healthcare provider facilities are associated with), classification of the healthcare provider facility (e.g., classified based on average income of a population where the healthcare facility is located, classified based on an urban to rural scale, etc.), etc.), individual healthcare provider data (e.g., age of the individual healthcare provider, gender of the individual healthcare provider, race of the individual healthcare provider, languages spoken by the individual healthcare provider, specialties of the individual healthcare provider, certifications of the individual healthcare provider, educational background of the individual healthcare provider, years of experience of the individual healthcare provider, member satisfaction ratings of the individual healthcare provider, cost information of the individual healthcare provider, efficiency of the individual healthcare provider (e.g., information of if patients have to repeat visits), reviews of the individual healthcare provider, quality of care ratings of the individual healthcare providers, affiliation data (e.g., what healthcare provider facilities are associated with the individual healthcare providers, etc.), population data (e.g., average income, poverty levels, housing information, etc. of a population of a geographic area), etc.), and census data.

At block 425, the one or more processors 120 build the healthcare provider network by inputting the potential healthcare provider data into the trained machine learning algorithm (e.g., the one or more processors 120 applies the trained machine learning algorithm).

In some embodiments, the application of the trained machine learning algorithm at block 425 includes optimizing metrics to determine the healthcare provider network. For example, any of the optimized metrics may correspond to the categories of data shown in FIG. 3 (e.g., cost, quality of care, competitor network affiliation, population data, geographic data, access standards data, etc.).

Furthermore, advantageously, the healthcare provider network may be built by optimizing advantages gained from affiliations between entities. For example, there may be: (i) affiliations between individual healthcare providers, (ii) affiliations between healthcare facilities, (iii) affiliations between healthcare organizations, and/or (iv) affiliations between any of the individual healthcare providers, the healthcare facilities, and/or the healthcare organizations. For example, the machine learning algorithm may be more likely to bring in an individual healthcare provider if that individual healthcare provider is strongly affiliated with another individual healthcare provider having desirable metrics (e.g., a high quality of care metric and/or cost efficiency metric).

The affiliations may be represented as a score based on how closely one entity is associated with another entity. For example, if doctors (e.g., individual healthcare providers) frequently refer patients to each other, they may be closely affiliated with each other, and thus have a high affiliation score. In some embodiments, the affiliation score is based on the strength of an edge/connection of nodes of the machine learning algorithm (e.g., shown in 230 of FIG. 2). In some such embodiments, a graph database is used to capture the relationships between nodes.

However, the affiliations may also be a binary indication of association (e.g., Dr. Bob is employed by Cleveland Clinic). In some examples, the machine learning algorithm includes individual healthcare providers in the healthcare provider network based on their affiliation with healthcare provider facilities and/or healthcare organizations (e.g., the machine learning algorithm does not include Dr. Bob in the healthcare provider network because Cleveland Clinic is not included in the network).

It should be understood that not all blocks of the example flowcharts 200, 400 are required to be performed. Moreover, the example flowcharts 200, 400 are not mutually exclusive (e.g., block(s)/event(s) from each example flowchart 200, 400 may be performed in any particular implementation).

Additional Exemplary Embodiments

Aspect 1. A computer-implemented method for building a healthcare provider network, the method comprising:

receiving, via one or more processors, historical healthcare provider data;

training, via the one or more processors, a machine learning algorithm based on the historical healthcare provider data;

receiving, via the one or more processors, potential healthcare provider data, the potential healthcare provider data including data of individual healthcare providers, and healthcare provider facilities; and building, via the one or more processors, a healthcare provider network by inputting the potential healthcare provider data into the trained machine learning algorithm.

Aspect 2. The computer-implemented method of aspect 1, wherein the healthcare provider network includes individual healthcare providers having individual healthcare provider types, and wherein the individual healthcare provider types include:

a primary care provider (PCP);

a cardiologist;

a radiologist;

a pediatrician;

a dermatologist;

a pulmonologist; and/or an oncologist.

Aspect 3. The computer-implemented method of any one of aspects 1-2, wherein the trained machine learning algorithm builds the healthcare provider network to include a disproportionately large number of PCP providers compared to other healthcare provider types.

Aspect 4. The computer-implemented method of any one of aspects 1-3, wherein the healthcare provider network includes healthcare provider facilities having healthcare provider facility types, and wherein the healthcare provider facility types include:

a hospital;

a primary care provider (PCP) office;

a laboratory;

an urgent care facility; and/or an addiction treatment facility.

Aspect 5. The computer-implemented method of any one of aspects 1-4, wherein the training comprises:

applying a search algorithm to identify mini healthcare provider networks in the historical healthcare provider data; and training the machine learning algorithm based on the identified mini healthcare provider networks.

Aspect 6. The computer-implemented method of any one of aspects 1-5, wherein:

the healthcare provider network has a type of a Medicare network, a Medicaid network, or an exchange network; and the trained machine learning algorithm builds the healthcare provider network based on the healthcare provider network type.

Aspect 7. The computer-implemented method of any one of aspects 1-6, wherein:

the healthcare provider network has an organization type of health maintenance organization (HMO), or preferred provider organization (PPO); and the trained machine learning algorithm builds the healthcare provider network based on the organization type.

Aspect 8. The computer-implemented method of any one of aspects 1-7, wherein the healthcare provider network is a single tier network.

Aspect 9. The computer-implemented method of any one of aspects 1-8, wherein the healthcare provider network is a tiered network.

Aspect 10. The computer-implemented method of any one of aspects 1-9, wherein the trained machine learning algorithm builds the healthcare provider network by optimizing a cost efficiency metric, and/or a quality of care metric.

Aspect 11. The computer-implemented method of any one of aspects 1-10, wherein:

the healthcare provider network includes a plurality of individual healthcare providers, and a plurality of healthcare organizations; and the trained machine learning algorithm builds the healthcare provider network based on affiliations between individual healthcare providers of the plurality of healthcare providers, and healthcare organizations of the plurality of healthcare organizations.

Aspect 12. The computer-implemented method of any one of aspects 1-11, wherein:

the potential healthcare provider data includes data of individual healthcare providers; and the building of the healthcare provider network comprises:

(i) identifying, in the potential healthcare provider data: (a) relationships between individual healthcare providers, and (b) strengths of the relationships between individual healthcare providers; and (ii) building the healthcare provider network based on the identified relationships and strengths of the relationships.

Aspect 13. The computer-implemented method of any one of aspects 1-12, wherein the historical healthcare provider data includes healthcare facilities classified based on an urban to rural scale.

Aspect 14. The computer-implemented method of any one of aspects 1-13, wherein:

the historical healthcare provider data includes healthcare facilities classified based on population incomes of geographic areas that the healthcare facilities are located in; and the training of the machine learning algorithm comprises including a requirement that a healthcare provider network built by the machine learning algorithm include a higher density of healthcare facilities for a geographic area with a lower income population than a density of healthcare facilities for a geographic area with a higher income population.

Aspect 15. The computer-implemented method of any one of aspects 1-14, wherein:

the training of the machine learning algorithm comprises including a requirement that a healthcare provider network built by the machine learning algorithm include a higher healthcare facility density for a geographic area with higher population density than for a geographic area with a lower population density.

Aspect 16. The computer-implemented method of any one of aspects 1-15, wherein the training comprises:

assigning, in the historical data, cost efficiency metrics to individual healthcare providers based on readmission rates, and/or number of recommended tests.

Aspect 16a. The computer-implemented method of any one of aspects 1-16, wherein the machine learning algorithm is further trained based on forecasted data.

Aspect 17. A computer-implemented method for building a healthcare provider network, the method comprising:

receiving, via the one or more processors, potential healthcare provider data, the potential healthcare provider data including data of individual healthcare providers, and healthcare provider facilities; and building, via the one or more processors, a healthcare provider network by inputting the potential healthcare provider data into the trained machine learning algorithm, wherein the built healthcare provider network includes individual healthcare providers and healthcare provider facilities.

Aspect 18. The computer-implemented method of aspect 17, wherein the individual healthcare providers of the built healthcare provider network have individual healthcare provider types, and wherein the individual healthcare provider types include:

a primary care provider (PCP);

a cardiologist;

a radiologist;

a pediatrician;

a dermatologist;

a pulmonologist; and/or an oncologist.

Aspect 19. A computer system configured to build a healthcare provider network, the computer system comprising one or more processors configured to:

receive historical healthcare provider data;

train a machine learning algorithm based on the historical healthcare provider data;

receive potential healthcare provider data, the potential healthcare provider data including data of individual healthcare providers, and healthcare provider facilities; and build a healthcare provider network by inputting the potential healthcare provider data into the trained machine learning algorithm.

Aspect 20. The computer system of aspect 19, wherein the one or more processors are further configured to use the trained machine learning algorithm to build the healthcare provider network by optimizing a cost efficiency metric, and/or a quality of care metric.

OTHER MATTERS

Although the text herein sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '______' is hereby defined to mean . . . " or a similar sentence, there is no intent to limit the meaning of that term, either expressly or by implication, beyond its plain or ordinary meaning, and such term should not be interpreted to be limited in scope based upon any statement made in any section of this patent (other than the language of the claims). To the extent that any term recited in the claims at the end of this disclosure is referred to in this disclosure in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based upon the application of 35 U.S.C. § 112(f).

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations). A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment may be included in at least one embodiment.

The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

Upon reading this disclosure, those of skill in the art will appreciate still additional alternative structural and functional designs for the approaches described herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

It is therefore intended that the foregoing detailed description be regarded as illustrative rather than limiting, and that it be understood that it is the following claims, including all equivalents, that are intended to define the spirit and scope of this invention.

Furthermore, the patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed:

1. A computer-implemented method for building a healthcare provider network, the method comprising:

receiving, via one or more processors, historical healthcare provider data;

training, via the one or more processors, a machine learning algorithm based on the historical healthcare provider data, wherein the training comprises:

applying a search algorithm to identify mini healthcare provider networks in the historical healthcare provider data by optimizing an objective cost function along at least one dimension including: a competitor network affiliation dimension, a population data dimension, or a geographic data dimension, wherein the identified mini healthcare provider networks are from sections of cities; and training the machine learning algorithm by inputting the identified mini healthcare provider networks into the machine learning algorithm;

receiving, via the one or more processors, potential healthcare provider data, the potential healthcare provider data including data of individual healthcare providers, and healthcare provider facilities; and building, via the one or more processors, a healthcare provider network by: (i) inputting the potential healthcare provider data into the trained machine learning algorithm, and (ii) optimizing at least one metric, the at least one metric including: a competitor network affiliation, population data, or geographic data; and wherein the mini healthcare provider networks are smaller than the healthcare provider network.

2. The computer-implemented method of claim 1, wherein the healthcare provider network includes individual healthcare providers having individual healthcare provider types, and wherein the individual healthcare provider types include:

a primary care provider (PCP);

a cardiologist;

a radiologist;

a pediatrician;

a dermatologist;

a pulmonologist; and/or an oncologist.

3. The computer-implemented method of claim 2, wherein the trained machine learning algorithm builds the healthcare provider network to include a disproportionately large number of PCP providers compared to other healthcare provider types.

4. The computer-implemented method of claim 1, wherein the healthcare provider network includes healthcare provider facilities having healthcare provider facility types, and wherein the healthcare provider facility types include:

a hospital;
a primary care provider (PCP) office;
a laboratory;
an urgent care facility; and/or
an addiction treatment facility.

5. The computer-implemented method of claim 1, wherein:

the healthcare provider network has a type of a Medicare network, a Medicaid network, or an exchange network; and the trained machine learning algorithm builds the healthcare provider network based on the healthcare provider network type.

6. The computer-implemented method of claim 1, wherein:

the healthcare provider network has an organization type of health maintenance organization (HMO), or preferred provider organization (PPO); and the trained machine learning algorithm builds the healthcare provider network based on the organization type.

7. The computer-implemented method of claim 1, wherein the healthcare provider network is a single tier network.

8. The computer-implemented method of claim 1, wherein the healthcare provider network is a tiered network.

9. The computer-implemented method of claim 1, wherein:

the healthcare provider network includes a plurality of individual healthcare providers, and a plurality of healthcare organizations; and the trained machine learning algorithm builds the healthcare provider network based on affiliations between individual healthcare providers of the plurality of healthcare providers, and healthcare organizations of the plurality of healthcare organizations.

10. The computer-implemented method of claim 1, wherein:

the potential healthcare provider data includes data of individual healthcare providers; and the building of the healthcare provider network comprises:

(i) identifying, in the potential healthcare provider data: (a) relationships between individual healthcare providers, and (b) strengths of the relationships between individual healthcare providers; and (ii) building the healthcare provider network based on the identified relationships and strengths of the relationships.

11. The computer-implemented method of claim 1, wherein the historical healthcare provider data includes healthcare facilities classified based on an urban to rural scale.

12. The computer-implemented method of claim 1, wherein:

the historical healthcare provider data includes healthcare facilities classified based on population incomes of geographic areas that the healthcare facilities are located in; and the training of the machine learning algorithm comprises including a requirement that a healthcare provider network built by the machine learning algorithm include a higher density of healthcare facilities for a geographic area with a lower income population than a density of healthcare facilities for a geographic area with a higher income population.

13. The computer-implemented method of claim 1, wherein:

the training of the machine learning algorithm comprises including a requirement that a healthcare provider network built by the machine learning algorithm include a higher healthcare facility density for a geographic area with higher population density than for a geographic area with a lower population density.

14. The computer-implemented method of claim 1, wherein the training comprises:

assigning, in the historical data, cost efficiency metrics to individual healthcare providers based on readmission rates, and/or number of recommended tests.

15. A computer-implemented method for building a healthcare provider network, the method comprising:

receiving, via one or more processors, potential healthcare provider data, the potential healthcare provider data including data of individual healthcare providers, and healthcare provider facilities; and building, via the one or more processors, a healthcare provider network by: (i) inputting the potential healthcare provider data into a machine learning algorithm, and (ii) optimizing at least one metric, the at least one metric including: a competitor network affiliation, population data, or geographic data, wherein the built healthcare provider network includes individual healthcare providers and healthcare provider facilities;

wherein the machine learning algorithm is trained by:

applying a search algorithm to identify mini healthcare provider networks in historical healthcare provider data by optimizing an objective cost function along at least one dimension including: a competitor network affiliation dimension, a population data dimension, or a geographic data dimension, wherein the identified mini healthcare provider networks are from sections of cities; and training the machine learning algorithm by inputting the identified mini healthcare provider networks into the machine learning algorithm; and wherein the mini healthcare provider networks are smaller than the healthcare provider network.

16. The computer-implemented method of claim 15, wherein the training the machine learning algorithm by inputting the identified mini healthcare provider networks into the machine learning algorithm occurs on a graphics processing unit (GPU) included in the one or more processors, and wherein the individual healthcare providers of the built healthcare provider network have individual healthcare provider types, and wherein the individual healthcare provider types include:

a primary care provider (PCP);
a cardiologist;
a radiologist;
a pediatrician;
a dermatologist;
a pulmonologist; and/or
an oncologist.

17. A computer system configured to build a healthcare provider network, the computer system comprising one or more processors configured to:

receive historical healthcare provider data;

train a machine learning algorithm based on the historical healthcare provider data, wherein the one or more processors are configured to train the machine learning algorithm by:

applying a search algorithm to identify mini healthcare provider networks in the historical healthcare provider data by optimizing an objective cost function along at least one dimension including: a competitor network affiliation dimension, a population data dimension, or a geographic data dimension, wherein the identified mini healthcare provider networks are from sections of cities; and training the machine learning algorithm by inputting the identified mini healthcare provider networks into the machine learning algorithm;

receive potential healthcare provider data, the potential healthcare provider data including data of individual healthcare providers, and healthcare provider facilities; and build a healthcare provider network by: (i) inputting the potential healthcare provider data into the trained machine learning algorithm, and (ii) optimizing at least one metric, the at least one metric including: a competitor network affiliation, population data, or geographic data; and wherein the mini healthcare provider networks are smaller than the healthcare provider network.

18. The computer-implemented method of claim 1, wherein:

the search algorithm comprises a depth-first search algorithm or a breadth-first search algorithm; and the method further comprises recommending the built healthcare provider network to an insurance company.

19. The computer-implemented method of claim 1, wherein the training the machine learning algorithm based on the historical healthcare provider data further includes iteratively comparing output of the machine learning algorithm to the identified mini healthcare provider networks.

20. The computer system of claim 17, wherein:

the at least one metric includes all of the: competitor network affiliation, population data, and geographic data; and the applying a search algorithm to identify the mini healthcare provider networks includes optimizing the objective cost function along all of the competitor network affiliation dimension, the population data dimension, and the geographic data dimension.

* * * * *